(12) United States Patent
Engel et al.

(10) Patent No.: US 9,296,685 B2
(45) Date of Patent: Mar. 29, 2016

(54) METHOD OF PRODUCING NANOPARTICLE SUSPENSIONS

(75) Inventors: Robert Engel, Speyer (DE); Wolfgang Gerlinger, Limburgerhof (DE); Stefan Braese, Troisdorf (DE); Thierry Muller, Strassburg (FR); Christina Belenki, Karlsruhe (DE); Heike P. Schuchmann, Stutensee (DE); Marion Gedrat, Karlsruhe (DE)

(73) Assignee: BASF SE, Ludwigshafen (DE)

( * ) Notice: Subject to any disclaimer, the term of this patent is extended or adjusted under 35 U.S.C. 154(b) by 689 days.

(21) Appl. No.: 13/583,536

(22) PCT Filed: Mar. 7, 2011

(86) PCT No.: PCT/IB2011/050942
§ 371 (c)(1),
(2), (4) Date: Sep. 10, 2012

(87) PCT Pub. No.: WO2011/110990
PCT Pub. Date: Sep. 15, 2011

(65) Prior Publication Data
US 2012/0329888 A1    Dec. 27, 2012

Related U.S. Application Data

(60) Provisional application No. 61/311,433, filed on Mar. 8, 2010.

(30) Foreign Application Priority Data

Mar. 8, 2010 (EP) ..................... 10002361

(51) Int. Cl.
| | |
|---|---|
| *C07C 69/36* | (2006.01) |
| *C07C 271/08* | (2006.01) |
| *B01F 17/00* | (2006.01) |
| *C07C 69/38* | (2006.01) |
| *C07C 233/56* | (2006.01) |

(52) U.S. Cl.
CPC ........... *C07C 271/08* (2013.01); *B01F 17/0007* (2013.01); *B01F 17/0021* (2013.01); *C07C 69/36* (2013.01); *C07C 69/38* (2013.01); *C07C 233/56* (2013.01)

(58) Field of Classification Search
CPC ...... C07C 69/36; C07C 69/38; C07C 233/56; C07C 271/08
USPC ............................. 516/22; 560/20, 157, 190
See application file for complete search history.

(56) References Cited

U.S. PATENT DOCUMENTS

| | | | |
|---|---|---|---|
| 3,510,508 A * | 5/1970 | Blachere et al. | ............... 560/43 |
| 4,160,077 A | 7/1979 | Brooks et al. | |
| 4,160,866 A | 7/1979 | Brooks et al. | |
| 5,571,442 A | 11/1996 | Masaki et al. | |
| 2007/0178144 A1 | 8/2007 | Hameyer | |
| 2010/0080898 A1 | 4/2010 | Danner et al. | |

FOREIGN PATENT DOCUMENTS

| | | |
|---|---|---|
| CN | 1251137 A | 4/2000 |
| CN | 101541415 | 9/2009 |
| EP | 1 008 655 A1 | 6/2000 |
| JP | 7-211350 A | 8/1995 |
| JP | 8-209543 A | 8/1996 |
| JP | 8 283530 | 10/1996 |
| JP | 2007-203288 A | 8/2007 |

OTHER PUBLICATIONS

International Search Report Issued Jun. 16, 2011 in PCT/IB11/50942 Filed Mar. 7, 2011.
International Preliminary Report on Patentability issued Jul. 19, 2012 in PCT/IB2011/050942.
Alfred R. Bader et al., "Transesterification. II. Esters of Strong Organic Acids", Journal of the American Chemical Society 1952, vol. 74, 3 pages.
K. Bartel et al., "Hypoiodite Reaction: the Decomposition of Oxalic Acid Half-esters", J. Chem. Soc., 1971, No. 20, 4 pages.

* cited by examiner

*Primary Examiner* — Edward Cain
(74) *Attorney, Agent, or Firm* — Oblon, McClelland, Maier & Neustadt, L.L.P.

(57) ABSTRACT

Method of producing a nanoparticle suspension with the steps (i) preparation of an emulsion of a disperse polar phase, where the aqueous phase comprises one or more precursor substances forming the nanoparticles, in a continuous organic phase in the presence of an emulsifier stabilizing the emulsion, (ii) conversion of the one or more precursor substances to nanoparticles in the disperse aqueous phase, (iii) breaking of the emulsion and phase separation, where the nanoparticle suspension is obtained as one phase, (iv) separation off of the nanoparticle suspension, (v) optionally isolation of the nanoparticles from the nanoparticle suspension, wherein the emulsifier is selected from compounds of the general formula (I) in which X is O, NH, Y is C(O), NH, R is a saturated or a mono- or polyunsaturated, linear or branched hydrocarbon radical having 6 to 30 carbon atoms and $R^1$ is hydrogen or $C_1$-$C_4$-alkyl, and $R^2$ is a saturated or a mono- or polyunsaturated, linear or branched hydrocarbon radical having 1 to 30 carbon atoms, preferably 6 to 30 carbon atoms, $R^3$ is $C_1$-$C_4$-alkyl, n is 0 or 1, and the breaking of the emulsion is effected by splitting the emulsifier.

(I)

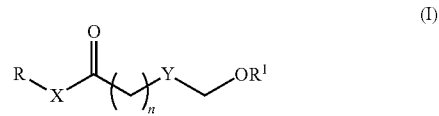

18 Claims, No Drawings

METHOD OF PRODUCING NANOPARTICLE SUSPENSIONS

The invention relates to a method of producing and/or functionalizing nanoparticle suspensions.

The miniemulsion method for the mass-transfer-controlled synthesis of nanoparticles includes the preparation of a water-in-oil miniemulsion (W/O miniemulsion), where a water-soluble reactant is introduced as initial charge in the disperse phase water. After the emulsifying step, the miniemulsion is admixed with the second, oil-soluble and partially water-soluble reactant, which then diffuses through the continuous phase via the interface occupied by emulsifier into the miniemulsion drops and thereby initiates the precipitation reaction (mass-transfer-controlled method). Following the precipitation reaction, a purification and/or conversion of the minisuspoemulsion into a suspension is required. In one variant, a water-in-oil emulsion comprising a first reactant can be mixed with a water-in-oil emulsion comprising a second reactant where, as a result of coalescence of the drops of the two disperse phases, the reactants present therein are reacted (coalescence-controlled method). Instead of the aqueous phase, it is also possible in each case for a polar organic phase, which is immiscible with the nonpolar continuous oil phase, to act as disperse phase.

WO8/058958 describes a method of producing a minisuspoemulsion of submicron core/shell particles in which
the starting point is a suspoemulsion of a first, disperse liquid phase I in a second, continuous liquid phase II which comprises
in the first, disperse liquid phase I nanoparticles of a solid K forming the core and
a molecularly disperse dissolved precursor substance for the shell and optionally a reactant, and
in the first, disperse liquid phase I of the suspoemulsion, the submicron core/shell nanoparticles are produced by chemical or physical conversion of the precursor substance for the shell.

Known methods for separating the suspoemulsion are (a) azeotropic distillation, (b) addition of solubility promoters and (c) filtration.

The azeotropic distillation brings about a removal of the more readily volatile phase and also a concentration of the nanosuspension through partial removal of the other phase. The removal of the aqueous phase can, however, lead to the crystallizing out of remaining precursor substance, which is then present in the suspension as particles and thus leads to contamination of the suspension. Moreover, it is an energy- and cost-intensive method. In addition, the method can only be carried out if the phase which is to comprise the nanoparticles, thus, for example the aqueous phase, has the higher boiling point.

The separation of emulsion into an oily and an aqueous phase (or more generally into a nonpolar and apolar phase) can furthermore take place by adding a solubility promoter which is soluble both in the aqueous phase and also in the oily phase. Isopropanol, acetone or demulsifiers, for example, can act as solubility promoters. A disadvantage is the dilution of the end product with the solubility promoter. Moreover, nanoparticles may be present both in the aqueous phase and also in the oily phase.

The separation of an emulsion laden with nanoparticles by filtration often proves difficult since the filter membrane has a tendency to become blocked as a result of fouling, which increases the filtration time. In order to keep the pressure drop low during the filtration, moreover, large filter areas need to be maintained.

The term emulsions is used to refer to liquid-disperse systems which consist of two immiscible liquid phases, of which the one phase, which is referred to as disperse or internal phase, is present in dispersed form in the second phase, referred to as continuous or homogeneous phase, in the form of fine droplets. Depending on the polarity of the phases, emulsions are referred to as oil-in-water (O/W) or water-in-oil (W/O) emulsions, where, in the first case, a hydrophobic oil phase, consisting of nonpolar media, is present, in the form of finely dispersed drops, in a polar phase consisting of an aqueous solution or other polar components immiscible with the nonpolar phase. In the case of the W/O emulsion, conversely, the polar phase is present in the form of finely dispersed drops in the nonpolar oil phase.

The term "miniemulsion" is used for thermodynamically unstable liquid-disperse systems (emulsions) stabilized kinetically by stearic and/or electrostatic effects and/or by one or more emulsifiers and/or by further auxiliaries, and the disperse phase of which has an average droplet diameter of <5000 nm (<5 µm).

The term suspoemulsion is used for systems which have solids particles distributed in an emulsion, and, accordingly, the term minisuspoemulsion for a miniemulsion with solids particles distributed therein.

It is a prerequisite of emulsification that the drops are adequately stable in the miniemulsion or in the suspoemulsion. Depending on the substance system, this can be provided as the result of surface charge, i.e. electrostatic propulsion of the drops themselves. If external stabilization of the drop phase by emulsifiers is required, then this can take place via electrostatic and/or stearic effects which are brought about by suitable stabilizing auxiliaries which are present in the continuous phase. Auxiliaries for stabilizing the particles and/or the emulsion may also be present in the disperse phase. Auxiliaries for stabilizing the miniemulsion or the submicron suspension also include substances which change the rheological properties of the continuous phase in such a way that coalescence, creaming or sedimentation of the drops or of the particles of the disperse phase are prevented or slowed.

It is an object of the invention to provide a method of producing nanoparticles or of functionalizing nanoparticles in a water-in-oil emulsion, in which the separation of the phase comprising the nanoparticles from the oily phase becomes particularly simple.

The object is achieved by a method of producing a nanoparticle suspension with the steps (i) preparation of an emulsion of a disperse polar phase, where the polar phase comprises one or more precursor substances forming the nanoparticles, in a continuous nonpolar phase in the presence of an emulsifier stabilizing the emulsion, (ii) conversion of the one or more precursor substances to nanoparticles in the disperse polar phase, (iii) breaking of the emulsion and phase separation, where at least one nanoparticle suspension is obtained as at least one phase, (iv) separation off of the nanoparticle suspension, (v) optionally isolation of the nanoparticles from the nanoparticle suspension, wherein the emulsifier is selected from compounds of the general formula (I)

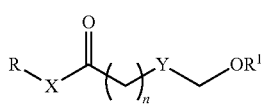

in which

X is O, NH, $NR^2$,

Y is C(O), NH, $NR^3$,

R is a saturated or a mono- or polyunsaturated, linear or branched hydrocarbon radical having 6 to 30 carbon atoms and $R^1$ is hydrogen or $C_1$-$C_4$-alkyl, and $R^2$ is a saturated or a mono- or polyunsaturated, linear or branched hydrocarbon radical having 1 to 30 carbon atoms, preferably 6 to 30 carbon atoms, $R^3$ is $C_1$-$C_4$-alkyl, n is 0 or 1, and the breaking of the emulsion is affected by splitting the emulsifier.

In formula (I), R is a saturated or a mono- or polyunsaturated, linear or branched hydrocarbon radical having 6 to 30, preferably 8 to 24 and particularly preferably 10 to 20, carbon atoms. Branches are also understood as meaning cycloaliphatic structures, for example cyclohexane rings, which may be present in the hydrocarbon radical. Preference is given to linear hydrocarbon radicals, and particular preference is given to saturated linear hydrocarbon radicals (linear alkyl radicals). Examples of linear alkyl radicals are decyl, dodecyl, tetradecyl, hexadecyl and octadecyl radicals.

$R^1$ is hydrogen or $C_1$-$C_4$-alkyl, for example methyl, ethyl, 1-propyl, 2-propyl and n-butyl, isobutyl, sec-butyl and tert-butyl. $R^3$ is $C_1$-$C_4$-alkyl, for example the radicals specified above.

$R^2$ is a saturated or a mono- or polyunsaturated, linear or branched hydrocarbon radical having 1 to 30, preferably 6 to 30, particularly preferably 8 to 24 and in particular 10 to 20, carbon atoms. Preference is given to linear hydrocarbon radicals, and particular preference is given to saturated linear hydrocarbon radicals (linear alkyl radicals). Examples of linear alkyl radicals are decyl, dodecyl, tetradecyl, hexadecyl and octadecyl radicals.

The invention also provides the emulsifiers themselves, as well as their use, in particular for stabilizing emulsions, preferably water-in-oil emulsions during the synthesis or functionalization of nanoparticles.

The continuous nonpolar phase is preferably a hydrocarbon or a mixture of hydrocarbons, for example an aromatic hydrocarbon or a mixture of aromatic hydrocarbons, an alkane or a mixture of alkanes, a vegetable oil or a mixture of vegetable oils, or a silicone oil or a mixture of silicone oils.

Preferably, the continuous phase has a low viscosity and thus a high diffusion coefficient. Particularly preferred organic solvents for use as continuous nonpolar phase are n-alkanes or cycloalkanes, for example n-decane, particular preference being given to n-decane, n-hexane, cyclohexane or n-dodecane, aromatic hydrocarbons, such as e.g. toluene or xylene, and also ethers such as e.g. tetrahydrofuran, or paraffins, waxes, mineral oils or vegetable oils. Particular preference is given to n-decane, white oil or Solvesso™.

The polar disperse phase may be an aqueous phase or a phase of a polar organic solvent. These must be essentially immiscible with the nonpolar organic phase. Suitable polar solvents are solvents completely miscible with water such as alcohols or polyols. Examples are methanol, ethanol, diethylene glycol, polyethylene glycol or more generally polyetherols. Mixtures of the polar solvents or mixtures of the polar solvents with water are also suitable as polar organic phase.

In one preferred embodiment of all of the variants of the method according to the invention described above, the disperse polar phase is an aqueous phase.

The preparation of a miniemulsion can take place, for example, with the introduction of mechanical energy, for example in the form of stirring energy, turbulent kinetic energy, ultrasound waves, pressure with subsequent decompression via a homogenization valve, by means of static mixers, micromixers or membranes or generally by impressing laminar or turbulent shear and/or extensional flows and cavitation.

To produce an emulsion with a narrow droplet size distribution and target drop size <1 μm, a high energy input is required, which can be introduced by rotor-stator systems, but preferably through high pressure. The rotor-stator systems used are, for example, toothed-wheel dispersing machines with rotational speeds in the range from 1000 to 20 000 revolutions per minute or colloid mills. During high-pressure homogenization, a coarsely disperse pre-emulsion is firstly compacted at the desired homogenization pressure (20 bar-2000 bar), pressed through a homogenizing nozzle and then decompressed. Examples of homogenizing nozzles which may be mentioned here are the radial nozzles, countercurrent nozzles (e.g. Microfluidizer®) and the simple perforated plate. An example of a suitable nozzle geometry is the countercurrent nozzle from Microfluidizer®. In one embodiment of the invention, firstly a coarsely disperse pre-emulsion of polar and nonpolar phase and emulsifier is prepared, for example by stirring using a propeller stirrer, and this is then homogenized using a Microfluidizer® at pressures Δp between 200 bar-1000 bar.

Through the extent of the energy input it is possible to adjust the drop size of the disperse phase and thus the particle size of the nanoparticles in a targeted manner. Preferred emulsifiers of the general formula (I) are oxalic acid esters of the general formula (Ia), oxamates of the general formula (Ib), hydroxycarbamates of the general formula (Ic) and malonic acid esters of the general formula (Id).

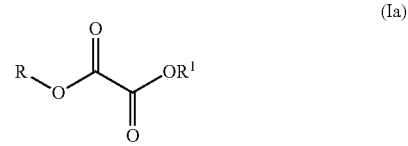

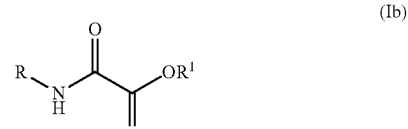

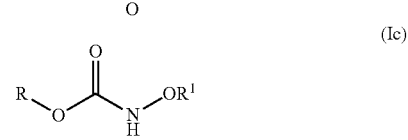

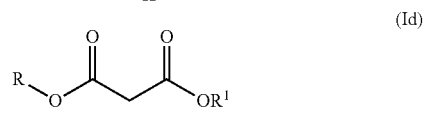

Here, R is a saturated or a mono- or polyunsaturated, linear or branched hydrocarbon radical having 6 to 30, preferably 8 to 24 and particularly preferably 10 to 20, carbon atoms. Preference is given to linear hydrocarbon radicals, and particular preference is given to saturated linear hydrocarbon radicals (linear alkyl radicals). Examples of linear alkyl radicals are decyl, dodecyl, tetradecyl, hexadecyl and octadecyl radicals.

Here, $R^1$ is furthermore hydrogen or $C_1$-$C_4$-alkyl, preferably hydrogen, methyl or ethyl, in particular hydrogen.

Particularly preferred emulsifiers are oxalic acid half-esters or malonic acid half-esters with $C_{10}$-$C_{14}$-alkanols, in particular n-decanol, n-dodecanol and n-tetradecanol.

The drops of the aqueous phase comprise one or more molecularly disperse dissolved precursor substances from which, optionally with participation by further reactants, as a result of reaction in the drops, the nanoparticles are formed. Here, the drops of the disperse aqueous phase act as minireactors on account of their small dimensions.

For this, the starting point is an emulsion of a first, disperse polar phase I in a second, continuous nonpolar phase II which comprises precursor substances forming nanoparticles in molecularly disperse dissolved form in the disperse polar phase I.

In one embodiment, the above emulsion additionally comprises one reactant. This may be present in dissolved form in the continuous nonpolar phase II or form the continuous nonpolar phase II.

Molecularly disperse dissolved precursor substances of the solid forming the nanoparticle which may be present in the first polar disperse phase may be organic or inorganic metal salts which can be converted to the corresponding metal oxides or mixed oxides through precipitation with a precipitating agent. Examples are inorganic or organic salts of tin, zinc, cerium, iron, zirconium, aluminum, hafnium, molybdenum, bismuth, copper, lead or copper or mixtures of the specified salts.

Molecularly disperse dissolved precursor substances of the solid forming the nanoparticles can furthermore be organic or inorganic metal salts which can be converted to the corresponding metals through reduction with a reducing agent. Examples are salts of Au, Ag, Ni, Pd, Fe, Sn, Co, Cu, Bi and Ce, which can be reduced to the corresponding colloidal metals or else to alloys of two or more of the specified metals.

The solids forming the nanoparticles may also be sheet silicates, $TiO_2$, ZnO, $SiO_2$, $Bi_2O_3$, $Fe_2O_3$, $CeO_x$, $MFe_xO_y$, where M is a transition metal or a main group metal, $ZrO_2$, SnO, $SnO_2$, $Al_xO_y$, CuO, $Cu_2O$, $CaCO_3$, or one or more semiconductors selected from sulfides and selenides, or silicon compounds. Suitable precursor substances are the corresponding metal salts, for example nitrates, carbonates, sulfates, halides (for example chlorides), acetates, and also salts of organic acids, such as lactates, carboxylates, carboxylic acids and hydroxy acids.

Furthermore, the solids forming the nanoparticles may be polymers, for example PET, polyacrylonitrile, polystyrene, polyketone, polycarbonate, PMMA, PU or polybutadiene terephthalate or polymer mixtures which are produced by polymerization by the method according to the invention.

The reactant or reactants may be, for example, a basic precipitating agent which converts the dissolved metal salts to their insoluble oxides. These may be bases that are soluble in organic solvents, in particular amines. Suitable amines soluble in nonpolar organic solvents are oleylamine and triethylamine. The basic precipitating agent may also be a water-soluble base, such as an aqueous sodium hydroxide or potassium hydroxide solution. In the case of preparing polymers, the reactants may be polymerization initiators that are soluble in nonpolar solvents.

The emulsion described above can be prepared in a first embodiment by
   starting from a solution of the precursor substance or precursor substances forming the nanoparticles in the polar phase I,
   adding the second, oily phase II and, while introducing energy, emulsifying with the first liquid phase I and then
   optionally adding further reactants and dissolving in molecularly disperse form, or altering the temperature in order to start the chemical and/or physical conversion in the drops of the disperse phases.

In a further embodiment, the above emulsion is prepared by
   starting from an emulsion of a first polar phase I as disperse phase which comprises, in dissolved form, precursor substances forming the nanoparticles, in the second, nonpolar phase II as continuous phase,
   introducing the reactant or the reactants in a third, polar phase III, which is miscible with the first, disperse polar phase I, but immiscible with the second, continuous nonpolar phase II, where
   an emulsion is formed from the third, polar phase III comprising the reactant or the reactants with a fourth, nonpolar phase IV, which is miscible with the second, nonpolar phase II, but not with the first and third polar phase I and III, with the introduction of energy, and
   the drops of the first, polar phase I and the drops of the third, polar phase III are brought to coalescence by introducing energy.

For example, the first, polar phase I comprises a metal salt which is soluble in this phase, whereas the third, polar phase III comprises a precipitating reagent which is soluble in this phase and which converts the soluble metal salt to an insoluble metal compound.

In one exemplary embodiment of the variant described above, barium chloride is introduced as initial charge as precursor substance dissolved in water as polar phase I. The emulsifier according to the invention is dissolved in n-decane as nonpolar phase II, and the crude emulsion obtained by stirring is then homogenized by means of two perforated plates with a pressure drop of about 100 to 1000 bar to give a miniemulsion. A water-soluble sulfate, e.g. sodium sulfate or ammonium sulfate, as reactant is likewise dissolved in water as polar phase III and preemulsified with n-decane comprising the emulsifier according to the invention as nonpolar phase IV. A miniemulsion is then prepared as described above by high-pressure homogenization. Both emulsions are mixed and the drops of the disperse phases are coalesced, for example by introducing mechanical energy. In the coalesced drops, the barium chloride and sulfate react to give insoluble barium sulfate, which precipitates out in finely disperse form.

In a further exemplary embodiment, the two miniemulsion as described above are prepared and mixed, the disperse polar phase I comprising a zinc oxide precursor compound and the disperse polar phase III comprising sodium hydroxide as basic precipitating reagent. By coalescing the drops of disperse phase I and III, zinc oxide precipitates out in finely disperse form.

In a further embodiment, the above emulsion is provided, this comprising one or more reactants in the drops of the disperse phase in addition to the molecularly disperse dissolved precursor substances for the nanoparticles, by
   adding the reactant or the reactants either dissolved in the second, continuous nonpolar phase II and diffusing them into the drops of the first, disperse polar phase I, or the reactant or the reactants forming the second continuous nonpolar phase, or adding them dissolved in a further nonpolar phase V which is miscible with the second, continuous nonpolar phase II, but not with the first disperse polar phase I, where the reactant or the reactants diffuse into the drops of the first, disperse polar phase I, or the reactant or the reactants form the nonpolar phase V, or adding them in a further polar phase V which is miscible with the first, disperse polar phase I, but not with the second, continuous nonpolar phase II.

For example, the first, polar phase I comprises a metal salt soluble in this phase, and a precipitating reagent soluble in the nonpolar continuous phase II is added directly to the emulsion of first phase I and second phase II. The precipitating reagent then diffuses from the continuous polar phase into the disperse phase and triggers the precipitation reaction.

In an exemplary embodiment of the variant described above, an aqueous barium chloride solution is introduced as polar phase I. The emulsifier according to the invention is dissolved in n-decane as nonpolar phase II and the two phases are preemulsified. The preemulsion is homogenized by high-pressure homogenization by means of two perforated plates with a pressure drop from 100 to 1000 bar to give a finely disperse miniemulsion. A sulfate soluble in the nonpolar phase II is then added through stirring and/or through addition to the emulsifying zone of the emulsifying apparatus. The sulfate diffuses from the continuous phase into the drops of the disperse phase, where upon barium sulfate nanoparticles precipitate out.

In a further exemplary embodiment, for example, zinc oxide and iron oxide precursor salts can be initially introduced in the polar phase I. After mixing with the nonpolar phase II, which comprises the emulsifier according to the invention, and producing the emulsion by means of high-pressure homogenization, an amine soluble in the nonpolar phase II, such as e.g. triethylamine, is added as further reactant and mixed in. The amine diffuses into the drops of the polar phase I, and so nanoparticles of zinc oxide and iron oxide precipitate out. Thus, in general, when using metal oxide precursors which precipitate out at different rates, it is possible to produce functionalized particles which have a core of the more rapidly precipitating metal oxide which is surrounded by particles or a shell of the metal oxide that precipitates out more slowly. If the metal oxides precipitate out at approximately the same rate, mixed oxide particles or a structure of particles present alongside one another are produced.

The reactant may also be a reducing agent soluble in an organic solvent or aqueous solvent. Examples thereof are $NaBH_4$, $LiAlH_4$ or organic reducing agents such as, for example, tetralin or alcohols.

The reactant may also be a gaseous reducing agent, for example hydrogen.

The disperse polar phase may be, for example, a waterglass solution which, as a result of lowering the pH or by removing water, solidifies to give silicon dioxide nanoparticles.

In a further aspect, the present invention relates to a method for functionalizing nanoparticles with the steps
(i) preparation of an emulsion (suspoemulsion) of a disperse polar phase, where the polar phase comprises nanoparticles in suspended form, in a continuous nonpolar phase in the presence of an emulsifier stabilizing the emulsion, where the polar and/or the nonpolar phase comprises one or more functionalization reagents in dissolved form,
(ii) reaction of the nanoparticles with the functionalization reagents in the disperse polar phase,
(iii) breaking of the emulsion and phase separation, where at least one nanoparticle suspension is obtained as at least one phase,
(iv) separation off of the nanoparticle suspension,
(v) optionally isolation of the functionalized nanoparticles, wherein the emulsifier is selected from compounds of the general formula (I)

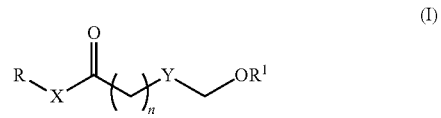

in which
X is O, NH,
Y is C(O), NH,
R is a saturated or a mono- or polyunsaturated, linear or branched hydrocarbon radical having 6 to 30 carbon atoms,
$R^1$ is hydrogen or $C_1$-$C_4$-alkyl, and
$R^2$ is a saturated or a mono- or polyunsaturated, linear or branched hydrocarbon radical having 1 to 30 carbon atoms, preferably 6 to 30 carbon atoms,
$R^3$ is $C_1$-$C_4$-alkyl, and
n is 0 or 1,
and the breaking of the emulsion is effected by splitting the emulsifier.

The drops of the first, disperse polar phase I can comprise both nanoparticles and also one or more molecularly disperse dissolved functionalization reagents. The functionalization reagents may also be present in dissolved form in the continuous phase and transfer to the drops of the disperse phase through diffusion. Here, the drops of the disperse aqueous phase act as mini reactors. Here, it is also ensured that the given polydispersity of the starting suspension of the nanoparticles is essentially retained.

The starting point for this can be a suspoemulsion of a first, disperse polar phase I in a second, continuous nonpolar phase II which comprises nanoparticles to be functionalized in the first disperse polar phase I and also one or more molecularly disperse dissolved functionalization reagents.

A further example of the functionalization of nanoparticles is the production of unclosed shells around the nanoparticles or of punctiform structures on the nanoparticles, which can be achieved through the nature of the reagents, by e.g. the reaction taking place directly on functional particles on the surface, or through the process procedure.

In one embodiment, the above suspoemulsion additionally comprises one reactant.

One example of the functionalization of nanoparticles is the production of core-shell particles, where the core consists of a first metal oxide and the shell consists of a second metal oxide.

For this, it is possible to start from a suspoemulsion of a first, disperse polar phase I in a second, continuous nonpolar phase II which comprises in the first, disperse polar phase I the cores of the core-shell particles as nanoparticles to be functionalized, and precursor substances forming the shell as one or more molecularly disperse dissolved functionalization reagents.

Suitable reactants R are the above-described basic precipitating agents, which may be precipitating agents soluble in organic solvents (amines) or bases soluble in aqueous solvents (alkali metal hydroxides).

The suspoemulsion described above can be produced in a first embodiment by starting from a suspension of the nanoparticles in the first, polar phase I, adding the functionalization reagent to this and dissolving it to give a molecularly disperse solution, and then adding the second, nonpolar phase II and emulsifying with the first, polar phase I with the introduction of energy.

In a further embodiment, the above suspoemulsion is produced by starting from a suspoemulsion of nanoparticles in the first, polar phase I as disperse phase in the second, nonpolar phase II as continuous phase, introducing the functionalization reagent in a third, polar phase III which is miscible with the first polar phase I, but immiscible with the second, nonpolar phase II, where an emulsion is formed from the third polar phase III comprising the functionalization reagent with a fourth nonpolar phase IV which is miscible with the second nonpolar phase II, but not with the first and the third polar phase I or III, with the introduction of energy, and the drops of the first polar phase I and the drops of the third, polar phase III are coalesced by introducing energy.

Thus, in this embodiment, the disperse phase of a first suspoemulsion, comprising the nanoparticles to be functionalized in the drops of the disperse phase is forced to coalesce with the disperse phase of a second emulsion comprising the functionalization reagent in the drops of the disperse phase. In one exemplary embodiment of the variant described above, titanium dioxide particles are initially introduced in a minisuspoemulsion comprising a disperse polar phase I and a continuous nonpolar phase II. The titanium dioxide particles can also be produced from titanium dioxide precursors in accordance with one of the methods specified above. A solution of palladium nitrate in water as third, polar phase III is emulsified with a mixture of n-decane as fourth, nonpolar phase IV and the emulsifier according to the invention, this emulsion is mixed with the suspominiemulsion, and the mixture is supplied with hydrogen. As a result of coalescence of the drops of the disperse phase of the two emulsions, the palladium nitrate passes into the drops with the nanoparticles. By reducing the palladium salt, metallic palladium is formed, which settles out in fine distribution on the titanium dioxide nanoparticles.

In a further embodiment, the above suspoemulsion is made available which comprises a reactant R in the drops of the disperse phase in addition to the nanoparticles and the molecularly disperse dissolved functionalization reagent. For this, the starting point is a suspoemulsion of nanoparticles and one or more molecularly disperse dissolved functionalization reagents in the first, polar phase I as disperse phase in the second, nonpolar phase II as continuous phase, where the reactant R is added either in the second, continuous nonpolar phase II and diffuses into the drops of the first, disperse polar phase I, or is added in a further polar phase V which is miscible with the first, disperse polar phase I, but not with the second, continuous nonpolar phase II, where an emulsion is formed from the further polar phase V, comprising the reactant R with an additional nonpolar phase VI, with the introduction of energy, and the drops themselves are forced to coalesce with the drops of the first, disperse polar phase I comprising the nanoparticles and also the functionalization reagents.

In a specific embodiment, for example, zinc oxide particles can be prepared by one of the aforementioned methods for producing nanoparticles in the presence of palladium nitrate. Alternatively, e.g. commercially available zinc oxide particles can be dispersed in palladium nitrate solution. Then, as described above, a miniemulsion is prepared and supplied with hydrogen or another reducing agent. The reducing agent diffuses into the drops via the continuous phase. By reducing the palladium nitrate, zinc oxide particles functionalized with palladium are formed.

In a further embodiment, the above suspoemulsion comprising, in addition to the nanoparticles, one or more molecularly disperse dissolved functionalization reagents, is produced through forced coalescence of the drops of a suspoemulsion comprising the nanoparticles and the reactant with the drops of a further emulsion comprising, in the drops of the disperse phase, the functionalization reagent or reagents.

The preparation of the suspoemulsion comprising the nanoparticles in the first disperse polar phase I with the second nonpolar phase II as continuous phase can be produced in a first embodiment by starting from a miniemulsion comprising a precursor substance for the nanoparticles in the first disperse polar phase I, where the second, nonpolar phase II is the continuous phase, and from which, through physical or chemical conversion of the precursor substance with the formation of nanoparticles, a minisuspoemulsion of the first disperse polar phase I comprising the nanoparticles in the second, nonpolar phase II as continuous phase is formed.

In a further embodiment, for this, the starting point is a miniemulsion comprising a precursor substance for the nanoparticles in the first disperse polar phase I, where the second nonpolar phase II is the continuous phase, after which a reactant is added either to the second, continuous nonpolar phase II and diffuses into the drops of the first, polar phase I, or is added in a third polar phase III which is miscible with the first polar phase I, but immiscible with the second nonpolar phase II, where an emulsion is formed from the third polar phase III comprising the reactant with a fourth nonpolar phase IV which is miscible with the second nonpolar phase II, but not with the first and the third polar phase I and III, with the introduction of energy, and is forced to coalesce with the drops of the first, disperse polar phase I comprising the precursor substance for the nanoparticles, and after which the precursor substance for the nanoparticles is chemically reacted with the reactant R.

The breaking of the emulsion is effected by splitting the emulsifier. The splitting of the emulsifier can take place by adding a base to the emulsion, by heating the emulsion or by irradiating the emulsion with UV light. As a result of the splitting, the emulsifier molecule loses its amphiphilic properties. The splitting can take place for example at the ester group or amide group, via which the hydrophobic hydrocarbon radical is bonded to the oxalate, oxalamide, carbamate or malonate group.

In one embodiment of the invention, the emulsifier is an oxalic acid ester of the general formula (Ia), and the splitting of the emulsifier is brought about by adding a base to the emulsion. Suitable bases are inorganic bases such as alkali metal hydroxides, for example sodium hydroxide and potassium hydroxide, which can be added as aqueous solutions, for example in concentrations of 0.1 to 2 molar. Here, mixing by gentle stirring may be adequate. The separation takes place within a few minutes and leads to the formation of two clearly separate phases.

In general, the polar phase comprises the nanoparticles. However, it is also possible for both phases to comprise nanoparticles.

In a further embodiment of the invention, the splitting of the emulsifier is brought about by heating the emulsion. In general, the emulsion is heated here to a temperature of 50 to 200° C., preferably 80 to 120° C.

In a further embodiment of the invention, the splitting of the emulsifier is brought about by irradiating the emulsion with UV light.

The phase separation into a polar phase and a nonpolar phase can take place by simply leaving the broken emulsion to stand.

If water is used as disperse polar phase, an aqueous phase comprising the nanoparticles is generally obtained as the lower phase, and a nonpolar phase essentially free of nanoparticles is obtained as the upper phase.

The nanoparticle suspension comprises solids preferably in a fraction of together 0.01 to 40% by weight, in particular in a fraction of from 5 to 30% by weight, based on the total weight of the nanoparticle suspension.

The particle size distribution can be determined in a manner known per se, for example using the method of static light scattering, dynamic light scattering or the analytical ultracentrifuge (see for example W. Mächtle, Makromolekulare Chemie 185 (1984), pages 1025 to 1039), but also using electron micrographs.

The nanoparticle suspensions can be used for example in printing processes, as pigments or for the catalytic coating of carrier materials. The nanoparticles can be isolated by evaporating the solvent in the suspension. However, the particles can also be isolated by centrifugation, repeated washing and centrifugation and optionally subsequent evaporation of remaining solvent.

EXAMPLES

Preparation of the Emulsifiers

One option is the reaction of an alcohol with an acid chloride to give the ester. Specifically, mention can be made of the Schotten-Baumann method, in which alcohols or amines are reacted with carbonyl chlorides in the presence of a stoichiometric amount of alkali metal hydroxide solution to give the corresponding esters or amides. The reaction conditions the purification can be found by the person skilled in the art without difficulties. Through an excess of oxalyl chloride, the formation of the diester of oxalic acid is counteracted.

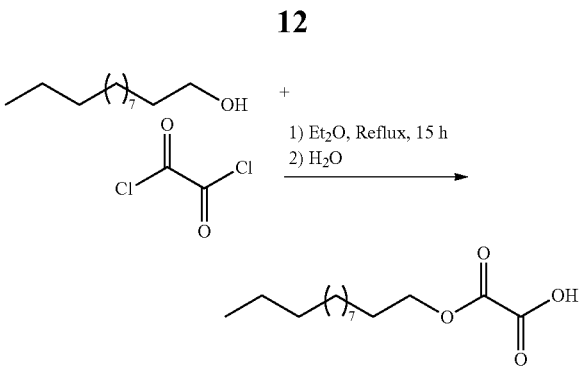

It has been found that when using only 3 equivalents of oxalyl chloride, a moderate yield of 63% of dodecyl oxalate is formed, which can be attributed to the formation of the diester of oxalic acid in a secondary reaction. Since the results reaction with 5 and 10 equivalents of oxalyl chloride with yields of 85 and 86%, respectively, of dodecyl oxalate are virtually no different, 5 equivalents were used for future reactions. Besides the excess of acid chloride, the order in which the starting materials are added to the reaction mixture is also decisive for the purity of the desired product. In order to avoid the formation of thermodynamically more stable oxalic diester as secondary reaction, through the slow dropwise addition of the dissolved alcohol in diethyl ether to oxalyl chloride, a very high excess of oxalyl chloride compared to the amount of alcohol should be achieved. Moreover, the reactivity of the oxalyl chloride was reduced by cooling the reaction mixture to 0° C. An extraction of the oily phase with aqueous ammonia solution was dispensed with since the oxalate does not dissolve in the aqueous phase on account of the lipophilic hydrocarbon chains. After optimizing the synthesis protocol using dodecanol, further aliphatic alcohols were reacted under the described reaction conditions to give oxalic monoesters.

Oxalic monoesters with shorter chains (C-8 to C-10) are oils that are viscous at room temperature; all other oxalates are white solids. During the syntheses, it was found that the reactivity of the alcohols decreases with increasing chain length of the carbon backbone. For this reason, the short-chain alcohols entered especially into secondary reactions, such as, for example, the formation of the corresponding oxalic diester. Moreover, it was shown that the synthesized oxalates do not have long-term stability. Over time, oxalic monoesters disproportionate to give oxalic acid and the corresponding oxalic diester according to

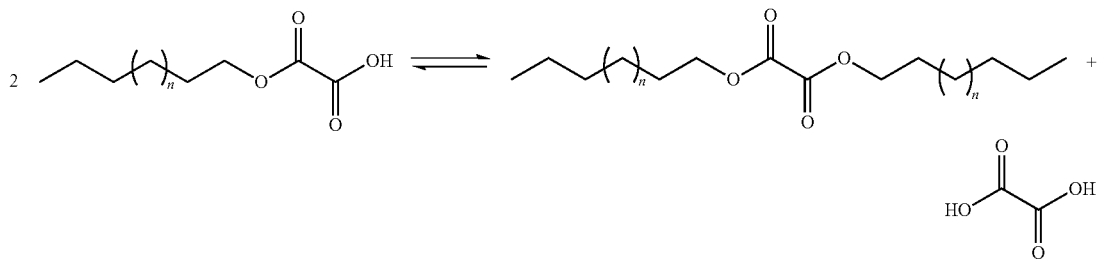

The stability of the monoesters increases with increasing length of the carbon chain. Those monoesters with a chain length up to 12 carbon atoms exhibit here a particularly high tendency towards formation of the respective diester. In contrast to this, octadecyl oxalate is very stable since even after several months, only a small amount of bisoctadecyl oxalate has been formed.

All oxalates were synthesized in good to very good yields. The sole exception is nonyl oxalate, which could only be obtained with a yield of 26%. In this case, the formation of bisnonyl oxalate dominated and approximately twice as much bisnonyl oxalate was formed as nonyl oxalate. Above a chain length of twelve carbon atoms, the yield is somewhat higher than in the case of shorter chains. Decyl oxalate is an exception since it can be obtained in 87% yield. This is due to the comparatively low reactivity of the alcohols with long carbon chains, as a result of which the selectivity increases and the formation of the corresponding diesters is suppressed. In the case of octadecyl oxalate, the yield is 89%; it is lower than for hexadecyl oxalate, which cannot be explained by the considerations hitherto. The reason for the lower yield here is the poor solubility of octadecyl oxalate in diethyl ether, which massively hinders the work-up. In general, the isolated yields depended on the reactivity of the starting materials and stability of the products. Moreover, in individual cases, the yield could be increased by slightly varying and optimizing the reaction conditions.

GPP 1: General preparation procedure for synthesizing oxalates 1.00 equivalent of the alcohol was dissolved in diethyl ether (8 ml per mmol of alcohol) and slowly added dropwise to 5.00 equivalents of the oxalyl chloride cooled to 0° C. The reaction mixture was firstly heated to room temperature and then heated under reflux overnight. The solvent and the excess oxalyl chloride were then removed under reduced pressure. The resulting oil was dissolved in diethyl ether and washed with water (6×3 ml per mmol of alcohol). The oily phase was dried over sodium sulfate and the solvent was removed under reduced pressure.

Example 1

Preparation of octyl oxalate

According to GPP 1, 0.630 ml of octanol (0.521 g, 4.00 mmol) were reacted with 1.72 ml of oxalyl chloride (2.54 g, 20.0 mmol). 0.724 g (3.58 mmol) of octyl oxalate was obtained as a yellowish oil. This comprises, as impurity that cannot be separated off, about 15% bisoctyl oxalate. Yield: 76%.–$^1$H-NMR (400 MHz, CDCl$_3$): δ (ppm)=0.86 (t, $^3$J=6.9 Hz, 3 H, CH$_3$), 1.20-1.40 (m, 10 H, 5×CH$_2$), 1.72 (tt, $^3$J=$^3$J=6.9 Hz, 2 H, OCH$_2$CH$_2$), 4.30 (t, $^3$J=6.9 Hz, 2 H, OCH$_2$), 9.67 (bs, 1 H, OH).–$^{13}$C-NMR (100 MHz, CDCl$_3$): δ (ppm)=14.0 (+, CH$_3$), 22.5 (−, C-7), 25.6 (−, CH$_2$), 28.1 (−, CH$_2$), 29.0 (−, 2×CH$_2$), 31.7 (−, CH$_2$), 68.1 (−, C-1), 158.0 ($C_{quart}$, COOH), 159.1 ($C_{quart}$, COO).

Example 2

Preparation of dodecyl oxalate

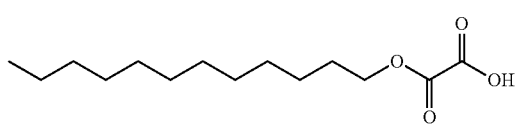 [SMILES: CCCCCCCCCCCCOC(=O)C(=O)O]

According to GPP 1, 3.61 g of dodecanol (19.4 mmol) were reacted with 8.30 ml of oxalyl chloride (12.3 g, 96.7 mmol). 4.38 g (17.0 mmol) of dodecyl oxalate were obtained as a white solid. Yield: 88%.–$^1$H-NMR (400 MHz, CDCl$_3$): δ (ppm)=0.87 (t, $^3$J=6.9 Hz, 3 H, CH$_3$), 1.24-1.39 (m, 18 H, 9×CH$_2$), 1.75 (tt, $^3$J=$^3$J=6.9 Hz, 2 H, OCH$_2$CH$_2$), 4.33 (t, $^3$J=6.9 Hz, 2 H, OCH$_2$), 8.65 (bs, 1 H, OH).–$^{13}$C-NMR (100 MHz, CDCl$_3$): δ (ppm)=14.1 (+, CH$_3$), 22.7 (−, C-11), 25.6 (−, CH$_2$), 28.2 (−, CH$_2$), 29.1 (−, CH$_2$), 29.3 (−, CH$_2$), 29.4 (−, CH$_2$), 29.5 (−, CH$_2$), 29.6 (−, 2×CH$_2$), 31.9 (−, CH$_2$), 68.3 (−, C-1), 158.0 ($C_{quart}$, COOH), 158.3 ($C_{quart}$, COO).–IR (DRIFT): 2919 [m, ν (C—H)], 2850 [m, ν (C—H)], 1755 [m, ν (C=O)], 1469 (w), 1181 [m, ν (C—O)], 720 (w) cm$^{-1}$.–El-MS m/z (%): 258 (2) [M$^+$], 213 (13), 185 (3), 168 (5), 140 (3), 111 (9), 97 (15), 92 (7), 83 (19), 69 (24), 55 (25), 43 (100) [C$_3$H$_7^+$].–HR-EIMS (C$_{14}$H$_{26}$O$_4$): calc. 258.1831. found 258.1828.–Elemental analysis C$_{14}$H$_{26}$O$_4$ (258): calc. C, 65.09: H, 10.14. found C, 64.50; H, 9.97.

Example 3

Preparation of tetradecyl N-hydroxycarbamate

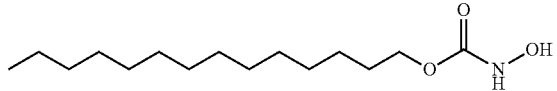 [SMILES: CCCCCCCCCCCCCCOC(=O)NO]

9.73 g of carbonyldiimidazole (26) (60.0 mmol, 3.00 equiv.) were dissolved in 250 ml of THF in a 500 ml round bottomed flask. 4.29 g of tetradecanol (6 g) (20.0 mmol, 1.00 equiv.) were added to this solution and the mixture was stirred for 20 h at room temperature. The reaction solution was then washed with in each case 100 ml of ammonium chloride solution and sodium chloride solution. The oily phase was dried over sodium sulfate and the solvent was removed under reduced pressure. The intermediate tetradecyl 1H-imidazole-1-carboxylate (31 b) was reacted without further purification.

For this, the residue was dissolved in 150 ml of pyridine, admixed with 4.17 g of hydroxylamine hydrochloride (60.0 mmol, 3.00 equiv.) and stirred for 6 h at RT. The majority of the solvent was then removed under reduced pressure and the residue was dissolved in 250 ml of dichloromethane. The solution was washed with ammonium chloride solution (3×80 ml) and sodium chloride solution (80 ml). The oily phase was dried over sodium sulfate and the solvent was removed under reduced pressure. Following purification by column chromatography (Cy-Hex/EtOAc 3/1), 2.76 g (10.1 mmol) of tetradecyl N-hydroxycarbamate (33 b) was obtained in the form of a white solid. Yield: 51%.–m.p. 64-66° C.–R$_f$=0.31 (Cy-Hex/EtOAc 3/1)–$^1$H-NMR (400 MHz, CDCl$_3$): δ (ppm)=0.87 (t, $^3$J=6.8 Hz, 3 H, CH$_3$), 1.20-1.36 (m, 22 H, 11×CH$_2$), 1.62 (tt, $^3$J=$^3$J=6.8 Hz, 2 H, OCH$_2$CH$_2$), 4.13 (t, $^3$J=6.8 Hz, 2 H, OCH$_2$), 7.40 (s, 1 H, NH), 7.52 (s, 1 H, OH).–$^{13}$C-NMR (100 MHz, CDCl$_3$): δ (ppm)=14.1 (+, CH$_3$), 22.7 (−, C-13), 25.7 (−, CH$_2$), 28.8 (−, CH$_2$), 29.2 (−, CH$_2$), 29.3 (−, CH$_2$), 29.5 (−, CH$_2$), 29.6 (−, CH$_2$), 29.6 (−, 2×CH$_2$), 29.7 (−, CH$_2$), 29.7 (−, CH$_2$), 31.9 (−, CH$_2$), 66.5 (−, C-1), 159.8 ($C_{quart}$, COO).–IR (DRIFT): 3296 [m, ν (N—H), ν (O—H)], 2920 [m, ν (C—H)], 2850 [m, ν (C—H)], 1690 [m, ν (C=O)] cm$^{-1}$.–EI-MS m/z (%): 273 (1) [M$^+$], 85 (34), 71 (69), 57 (100) [C$_4$H$_9^+$].–HR-EIMS (C$_{15}$H$_{31}$NO$_3$): calc. 273.2304. found 273.2306.

Example 4

Preparation of ethyl N-hexadecyl oxamate

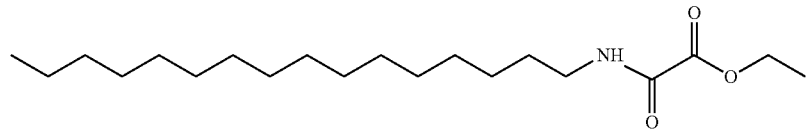 [SMILES: CCCCCCCCCCCCCCCCNC(=O)C(=O)OCC]

Under an argon atmosphere, 3.69 ml of ethyl oxalyl chloride (4.51 g, 33.0 mmol, 1.10 equiv.) were added dropwise to a solution, 0° C. cold, of 7.24 g of hexadecylamine (30.0 mmol, 1.00 equiv.) and 4.57 ml of triethylamine (3.34 g, 33.0 mmol, 1.10 equiv.) in 100 ml of absolute dichloromethane. The solution was brought to room temperature and stirred for 3 h. The reaction was then quenched with water (25 ml). The oily phase was washed with 1 m HCl (50 ml), with $NaHCO_3$ solution (50 ml) and then with water (50 ml). The oily phase was then dried over sodium sulfate and the solvent was removed under reduced pressure. 8.53 g (25.0 mmol) of ethyl N-hexadecyloxamate were obtained as a white solid. Yield: 83%.—m.p. 59-60.—$R_f$=0.73 (Cy-Hex/EtOAc 1/1)—$^1$H-NMR (400 MHz, $CDCl_3$): δ (ppm)=0.84 (t, $^3J$=6.7 Hz, 3 H, $CH_2CH_2CH_3$), 1.70-1.32 (m, 26 H, 13×$CH_2$), 1.35 (t, $^3J$=7.1 Hz, 3 H, $OCH_2CH_3$), 1.53 (tt, $^3J$=$^3J$=7.0 Hz, 2 H, $NHCH_2CH_2$), 3.30 (dt, $^3J$=$^3J$=7.0 Hz, 2 H, $NHCH_2$), 4.33 (q, $^3J$=7.1 Hz, $OCH_2$), 7.14 (s, 1 H, NH).—$^{13}$C-NMR (100 MHz, $CDCl_3$): δ (ppm)=13.9 (+, C-2), 14.1 (+, C-16▯), 22.6 (−, C-15▯), 26.7 (−, $CH_2$), 29.0 (−, $CH_2$), 29.1 (−, $CH_2$), 29.3 (−, $CH_2$), 29.4 (−, $CH_2$), 29.5 (−, $CH_2$), 29.5 (−, $CH_2$), 29.6 (−, 2×$CH_2$), 29.6 (−, 3×$CH_2$), 31.8 (−, $CH_2$), 39.9 (−, C-1▯), 63.0 (−, C-1), 156.4 ($C_{quart}$, CONH), 160.8 ($C_{quart}$, COO).—IR (DRIFT): 3345 [m, v (O—H)], 2914 [m, v (C—H)], 2850 [m, v (C—H)], 1677 [m, v (C=O)] $cm^{-1}$.—EI-MS m/z (%): 341 (2) [$M^+$], 268 (36), 58 (40), 43 (100) [$C_3H_7^+$].—HR-EIMS ($C_{20}H_{39}NO_3$): calc. 341.2930. found 341.2929.—Elemental analysis $C_{20}H_{39}NO_3$ (341): calc. N, 4.10; C, 70.33; H, 11.51. found N, 3.86; C, 70.29; H, 11.23.

Example 5

Preparation of N-hexadecyl oxamate

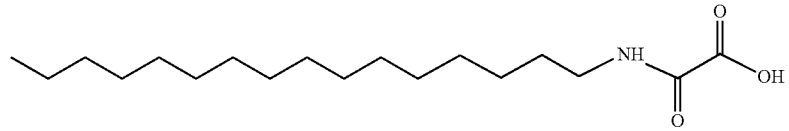 [SMILES: CCCCCCCCCCCCCCCCNC(=O)C(=O)O]

A solution of 2.65 g of ethyl N-hexadecyl oxamate (7.75 mmol, 1.00 equiv.) in 150 ml of THF was mixed with a solution of 0.557 g of LiOH (23.3 mmol, 3.00 equiv.) in 150 ml of water and stirred overnight at room temperature. The reaction mixture was then admixed with 100 ml of diethyl ether and acidified with 1 m HCl. The oily phase was dried over sodium sulfate and the solvent was removed under reduced pressure. 2.30 g (7.34 mmol) of N-hexadecyl oxamate were obtained in the form of a white solid.

Yield: 95%.—m.p. 103° C.—$^1$H-NMR (400 MHz, $CDCl_3$): δ (ppm)=0.88 (t, $^3J$=6.5 Hz, 3H, $CH_3$), 1.20-1.36 (m, 26 H, 13×$CH_2$), 1.58 (tt, $^3J$=$^3J$=6.8 Hz, 2 H, $NHCH_2CH_2$), 3.36 (dt, $^3J$=$^3J$=6.8 Hz, 2 H, $NHCH_2$), 7.28 (s, 1H, NH).—$^{13}$C-NMR (100 MHz, $CDCl_3$): δ (ppm)=14.1 (+, $CH_3$), 22.7 (−, C-15), 26.7 (−, $CH_2$), 29.0 (−, $CH_2$), 29.1 (−, $CH_2$), 29.3 (−, $CH_2$), 29.4 (−, $CH_2$), 29.5 (−, $CH_2$), 29.7 (−, 6×$CH_2$), 31.9 (−, $CH_2$), 40.6 (−, C-1), 157.3 ($C_{quart}$, CONH), 159.8 ($C_{quart}$, COO).—IR (DRIFT): 3284 [m, v (N—H), v (O—H)], 2917 [m, v (C—H)], 2849 [m, v (C—H)], 1759 [m, v (C=O)], 1682 [m, v (C=O)] $cm^{-1}$.—EI-MS m/z (%): 313 (4) [$M^+$], 268 (100) [$C_{17}H_{34}NO^+$], 103 (14), 58 (19), 43 (59).—HR-EIMS ($C_{18}H_{35}NO_3$): calc. 313.2617. found 313.2615.

Example 6

Preparation of tetradecyl malonate

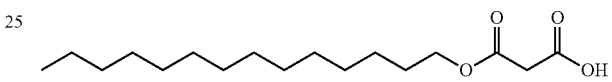

3.43 g of tetradecanol (16.0 mmol, 1.00 equiv.) and 2.31 g of Meldrum's acid (16.0 mmol, 1.00 equiv.) were introduced as initial charge in a 200 ml round bottomed flask and stirred at 120° C. for 3 h. After cooling to room temperature, the solid was washed with 20 ml of cold pentane. 3.32 g (11.1 mmol) of tetradecyl malonate were obtained as a white solid. Yield: 69%.—$^1$H-NMR (400 MHz, $CDCl_3$): δ (ppm)=0.87 (t, $^3J$=6.9 Hz, 3 H, $CH_3$), 1.22-1.37 (m, 22 H, 11×$CH_2$), 1.64 (tt, $^3J$=7.2Hz, $^3J$=6.8 Hz, 2H, $OCH_2CH_2$), 3.43 (s, 2 H, H-2), 4.17 (t, 6.8 Hz, 2 H, $OCH_2$), 10.83 (s, 1H, OH).—$^{13}$C-NMR (100 MHz, $CDCl_3$): δ (ppm)=14.1 (+, $CH_3$), 22.7 (−, C-13▯), 25.7 (−, $CH_2$), 28.4 (−, $CH_2$), 29.2 (−, $CH_2$), 29.3 (−, $CH_2$), 29.5 (−, $CH_2$), 29.5 (−, $CH_2$), 29.6 (−, $CH_2$), 29.6 (−, 2×$CH_2$), 29.7 (−, $CH_2$), 31.9 (−, $CH_2$), 40.6 (−, C-2), 66.2 (−, C-1▯), 167.1 ($C_{quart}$, C-3), 171.2 ($C_{quart}$, C-1).—IR (KBr): 2916 [m, v (C—H)], 2849 [m, v (C—H)], 1727 [m, v (C=O)] $cm^{-1}$.—EI-MS m/z (%): 301 (1) [$M+H^+$], 196 (13), 105 (100) [$C_3H_5O_4^+$], 83 (23), 43 (54).—HR-EIMS ($C_{17}H_{33}O_4$): calc. 301.2379. found 301.2382

Production of zinc oxide nanoparticles

The zinc oxide precursor used was zinc sulfate heptahydrate (Merck, Darmstadt), the basic precipitating agent used was the oil-soluble bases triethylamine (Merck Schuchardt OHG, Hohenbrunn) and oleylamine (Sigma-Aldrich, Steinheim). Zinc sulfate heptahydrate was introduced as initial charge in water. The zinc sulfate concentration of the aqueous phase was between 0.01 and 0.1 mol/l, preferably 0.1 mol/l.

The starting emulsion consisted of between 20 and 40 w/w-%, preferably 40 w/w-%, of aqueous zinc sulfate solution as disperse phase, 2 w/w-% of emulsifier and n-decane.

To produce an emulsion with a narrow drop size distribution and target drop size <1 μm, a high energy input is required, which can be introduced by means of rotor stator systems, but preferably by means of high pressure. During the high-pressure homogenization, a coarsely disperse preemulsion is firstly compacted to the desired homogenization pressure (20 bar-2000 bar), pressed through a homogenizing nozzle and then decompressed. Examples of homogenizing nozzles which may be mentioned here are the radial nozzle, the countercurrent nozzle (e.g. Microfluidizer®) and the simple perforated plate. The nozzle geometry relevant for this operation is the countercurrent nozzle from Microfluidizer®. Firstly, a premix consisting of n-decane, aqueous zinc sulfate solution and emulsifier was stirred for two minutes at 400 rpm using a propeller stirrer and then homogenized with the Microfluidizer® at pressures Op between 200 bar-1000 bar, preferably 1000 bar.

An oil-soluble base (triethylamine or oleylamine) was added to the stable emulsion with stirring. The emulsion was then stirred at 70° C. for 1 hour in order to ensure the transformation of zinc hydroxide to zinc oxide.

Comparative Example

Production of the emulsion using commercial emulsifiers
Composition of the Emulsion:
Disperse phase: 40 w/w-% 0.05 M zinc sulfate solution
Continuous phase: 58 w/w-% n-decane
Emulsifier: 2 w/w-% Glissopal® EM-23
Precipitating agent: oleylamine Firstly, a preemulsion was prepared by stirring the disperse phase, the continuous phase and the emulsifier for 2 minutes using a propeller stirrer. The resulting preemulsion was homogenized using a Microfluidizer® at ΔO=1000 bar. 30 ml of this emulsion were admixed with an equimolar amount of oleylamine, based on zinc sulfate, with stirring using a magnetic stirrer (200 rpm) and stirred for 2 minutes. The mixture was then further stirred for 60 minutes at 70° C.

The resulting suspoemulsion was then separated by (a) azeotropic distillation or (b) by adding solubility promoters or (c) by filtration.

(a) Separation by Azeotropic Distillation:

Azeotropic distillation here brings about a removal of the disperse phase water and also a concentration of the nanosuspension through partial removal of the continuous phase n-decane. The boiling point of the azeotropic water/n-decane mixture is 97.2° C. under atmospheric pressure.

The water phase and also some of the n-decane phase was removed on a rotary evaporator at 40° C. and 25 mbar. The zinc oxide particles present in the water drops of the emulsion are thus transferred to the n-decane phase. The removal of the aqueous phase likewise leads to the crystallizing out of the residual salt remaining during precipitation, which is then present in the suspension as particles. This leads to further contamination. The emulsifier remaining in the suspension stabilizes the nanoparticles, and targeted separation proves difficult. This method for purifying the emulsion can only be used if the oil-soluble reactant has a very low interfacial activity. The separation can accordingly only be realized when using triethylamine as the basic precipitating agent. When using oleylamine, a very interface-active reagent, a separating off of the aqueous phase cannot be carried out despite post-dilution with n-decane. Moreover, this is additionally a very energy-intensive and cost-intensive method.

(b) Separation by adding solubility promoters:

Following the precipitation reaction, the sample was admixed with one third of isopropanol, based on the emulsion volume, resulting in separation of the emulsion into an oily phase and an aqueous phase. The samples admixed with isopropanol were left to stand for 30 minutes in order to ensure complete separation of the two phases. An advantage of this method for separating the emulsion into the two starting phases is that two liquids with a clear phase separation are obtained. The residual salts remain in solution. A disadvantage, however, is the dilution of the end product. Moreover, nanoparticles were ascertained both in the n-decane phase and also in the water phase. Consequently, this method is only of limited suitability for separating the minisuspoemulsions.

(c) Separation by Filtration:

When separating a water/n-decane emulsion by filtration, it was pressed through a hydrophilic filter membrane with a pressure of 3 to 5 bar. At the hydrophilic membrane, the water drops of the emulsion spread and coalesce. Different filter membranes made of nitrocellulose, polycarbonates and nylon with drop sizes between 0.1 μm and 10 μm were used. The different membranes with different pore sizes were tested with emulsions stabilized with Glissopal® EM-23, PGPR and ER 190, where initially only experiments with emulsions without nanoparticles were carried out. However, it was possible to effect a separation only for an emulsion stabilized with ER 190 using a nylon membrane, pore size 0.2 μm and 0.8 μm. The separation of an emulsion laden with nanoparticles proved to be much more difficult. The membrane had an increased tendency towards blockage as a result of fouling, which increases the filtration time five-fold compared to particle-free emulsions. In view of the volume flows to be achieved, this method is not suitable as a scalable method for purifying minisuspensions.

Example 7

Preparation of the emulsion using the emulsifiers according to the invention
Composition of the Emulsion:
Disperse phase: 40 w/w-% 0.05 M zinc sulfate solution;
Continuous phase: 58 w/w-% n-decane;
Emulsifier: 2 w/w-% n-tetradecyl oxalate half-ester.
Precipitating Agent: Triethylamine Firstly, a preemulsion was prepared by stirring the disperse phase, the continuous phase and the emulsifier for two minutes using a propeller stirrer.

The resulting preemulsion was homogenized using a Microfluidizer at Δp=1000 bar. The Sauter diameter $x_{3,2}$ of the drops was 350 nm.

30 ml of this emulsion were admixed with triethylamine with stirring using a magnetic stirrer (200 rpm) and stirred for 2 minutes. The mixture is further stirred for 60 minutes at 70° C.

10 ml of 1 M sodium hydroxide solution were then added to the resulting suspoemulsion and roughly mixed in. After about two minutes, two clearly separate phases were obtained, and these were separated from one another by simple decantation.

In this way, it was possible to prepare an aqueous suspension of zinc oxide particles. The Sauter diameter of the particles was 36 nm, measured by means of the dynamic light scattering method.

Example 8

Production of palladium nanoparticles

The first, liquid phase consisted of 120 g of water and comprised 1 mmol/l of palladium nitrate, which was dissolved with stirring. The second, continuous phase consisted of a solution, prepared with stirring, of 3.3 percent by weight of n-tetradecyl oxalate half-ester in 175 g of n-decane. The two phases were preemulsified for 15 min using the Ultra-Turrax.

The resulting preemulsion was homogenized using a Microfluidizer at $\Delta p=1000$ bar. The Sauter diameter $x_{3,2}$ of the drops was 400 nm.

The miniemulsion was supplied with 5 bar of hydrogen for three hours with stirring.

The palladium nitrate was reduced to palladium by the hydrogen. The resulting suspoemulsion was then broken by adding and briefly stirring in 100 ml of one molar sodium hydroxide solution. Phase separation took place within a few minutes.

An aqueous suspension of palladium particles was obtained from this. The diameter of the palladium particles, determined via TEM micrographs, was 4-8 nm.

Example 9

Production of functionalized blackberry-like structured particles

Composition of the Suspension:

The first disperse liquid phase was prepared by dissolving 0.75 g of the surfactant Quadrol L® and 2.25 g of tin(II) chloride in 100 g of water with stirring. 0.75 g of surface-modified silicon dioxide particles were then added.

The second, continuous liquid phase was prepared by dissolving 2% by weight of n-tetradecyl oxalate half-ester in 200 g of n-decane with stirring.

The first disperse liquid phase and the second continuous liquid phase were preemulsified in an Ultra-Turrax® mixing device from IKA®-Werke GmbH & Co. KG (Staufen, Germany). The crude suspoemulsion prepared in this way was degassed by applying a vacuum.

This crude suspoemulsion was emulsified in a high-pressure homogenizer such that a drop size distribution with Sauter diameter $x_{3,2}$ of 530 nm was established. This fine emulsion was then degassed by applying a vacuum.

The precipitation was initiated by adding pyridine and heating to 90° C. The temperature was held for a further 5 hours with stirring.

The resulting suspoemulsion was then broken by adding and briefly stirring in 100 ml of 1 M sodium hydroxide solution. Phase separation took place within a few minutes.

In this way, it was possible to prepare a suspension of blackberry-like structured particles. Zinc dioxide settled out as 5 nm particles on the surface of the silicon dioxide core particles.

The liquids were separated off from the minisuspoemulsion of submicron core/shell particles obtained in this way in order to be able to make a High Angle Annular Dark Field-Scanning Transmission Electron Microscopy recording (HAADF-STEM recording).

Example 10

Production of nanoparticles by the coalescence-controlled method

The first, disperse liquid phase was produced by dissolving 6.5 g of barium chloride in 190 g of water with stirring. The second, continuous liquid phase was produced by dissolving 2% by weight of n-tetradecyl oxalate half-ester in 400 g of n-decane with stirring. The first, disperse liquid phase and the second, continuous liquid phase were preemulsified in an Ultra-Turrax® mixing device from IKA®-Werke GmbH & Co. KG (Staufen, Germany) and finely dispersed using a toothed-wheel dispersing machine at a rotational speed of 15 000 revolutions per minute.

The third, disperse liquid phase was produced by dissolving 4.4 g of sodium sulfate in 190 g of water with stirring. The fourth, continuous liquid phase was produced by dissolving 2% by weight of n-tetradecyl oxalate half-ester in 400 g of n-decane with stirring. The third, disperse liquid phase and the fourth, continuous liquid phase were preemulsified in an Ultra-Turrax® mixing device from IKA®-Werke GmbH & Co. KG (Staufen, Germany) and finely dispersed using a toothed-wheel dispersing machine at a rotational speed of 15 000 revolutions per minute.

The two miniemulsions were mixed. Using a toothed-wheel dispersing machine, the drops were forced to coalesce in order to initiate the precipitation of barium sulfate.

The resulting suspoemulsion was then broken by adding and briefly stirring in 100 ml of 1 M sodium hydroxide solution. The phase separation took place within a few minutes.

In this way, it was possible to prepare an aqueous suspension of barium sulfate particles. The particle sizes were determined using electron micrographs and are in the particle size range from 5 to 40 nm.

The invention claimed is:

1. A method of producing a nanoparticle suspension, the method comprising:
   (i) converting one or more precursor substances in an emulsion to nanoparticles in a disperse polar phase, wherein the disperse polar phase comprises the one or more precursor substances in a continuous nonpolar phase in the presence of an emulsifier stabilizing the emulsion;
   (ii) breaking the emulsion and phase separating the disperse polar phase to obtain at least one nanoparticle suspension as at least one phase, such that the breaking of the emulsion is effected by splitting the emulsifier;
   (iii) separating off the nanoparticle suspension; and
   (iv) optionally isolating nanoparticles from the nanoparticle suspension,
   wherein:
   the emulsifier is at least one compound of formula (I):

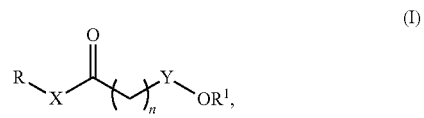

(I)

X is O, NH, or $NR^2$;
Y is C(O), NH, or $NR^3$;

R is a saturated or a mono- or polyunsaturated, linear or branched hydrocarbon radical having 6 to 30 carbon atoms;

$R^1$ is hydrogen or $C_1$-$C_4$-alkyl;

$R^2$ is a saturated or a mono- or polyunsaturated, linear or branched hydrocarbon radical having 1 to 30 carbon atoms;

$R^3$ is $C_1$-$C_4$-alkyl; and n is 0 or 1.

2. The method according to claim 1, wherein the emulsifier is selected from the group consisting of an oxalic acid ester of formula (Ia), an oxamate of formula (Ib), a hydroxycarbamate of formula (Ic), and malonic acid ester of formula (Id):

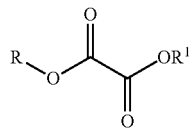
(Ia)

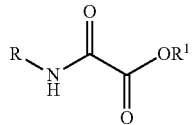
(Ib)

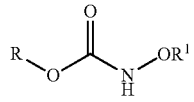
(Ic)

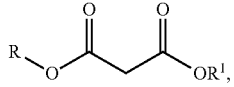
(Id)

wherein:

R is a saturated or a mono- or polyunsaturated, linear or branched hydrocarbon radical having 6 to 30 carbon atoms; and $R^1$ is hydrogen or $C_1$-$C_4$-alkyl.

3. The method according to claim 1, wherein the splitting of the emulsifier is effected by adding a base to the emulsion.

4. The method according to claim 3, wherein the emulsifier is an oxalic acid ester of formula (Ia):

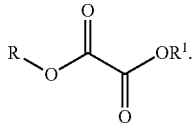
(Ia)

5. The method according to claim 1, wherein the splitting is effected by heating the emulsion to a temperature of from 50 to 200° C.

6. The method according to claim 1, wherein the nonpolar phase is a solvent selected from the group consisting of an n-alkane, an aromatic hydrocarbon, an ether, a paraffin, a wax, a mineral oil and a vegetable oil.

7. A method for functionalizing nanoparticles, the method comprising:

(i) reacting nanoparticles, in an emulsion of a disperse polar phase, with functionalization reagents in the disperse polar phase, wherein the disperse polar phase comprises the nanoparticles in suspended form in a continuous nonpolar phase in the presence of an emulsifier stabilizing the emulsion, such that the disperse polar phase, the continuous nonpolar phase, or both, comprise one or more functionalization reagents in dissolved form;

(ii) breaking the emulsion and phase separating the disperse polar phase to obtain, at least one nanoparticle suspension as at least one phase, such that the breaking of the emulsion is effected by splitting the emulsifier;

(iii) separating off the nanoparticle suspension; and (iv) optionally isolating functionalized nanoparticles, wherein:

the emulsifier is at least one compound of formula (I):

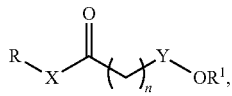
(I)

X is O, NH, or $NR^2$;

Y is C(O), NH, or $NR^3$;

R is a saturated or a mono- or polyunsaturated, linear or branched hydrocarbon radical having 6 to 30 carbon atoms;

$R^1$ is hydrogen or $C_1$-$C_4$-alkyl;

$R^2$ is a saturated or a mono- or polyunsaturated, linear or branched hydrocarbon radical having 1 to 30 carbon atoms;

$R^3$ is $C_1$-$C_4$-alkyl; and n is 0 or 1.

8. The method according to claim 7, wherein the emulsifier is selected from the group consisting of an oxalic acid ester of formula (Ia), an oxamate of formula (Ib), a hydroxycarbamate of formula (Ic), and a malonic acid ester of formula (Id):

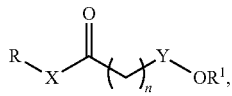
(Ia)

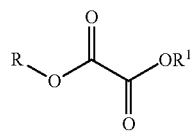
(Ib)

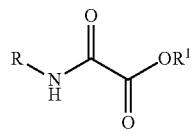
(Ic)

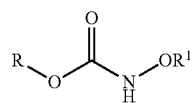
(Id)

wherein:

R is a saturated or a mono- or polyunsaturated, linear or branched hydrocarbon radical having 6 to 30 carbon atoms; and $R^1$ is hydrogen or $C_1$-$C_4$-alkyl.

9. The method according to claim 7, wherein the splitting of the emulsifier is carried out by adding a base to the emulsion.

10. The method according to claim 9, wherein the emulsifier is an oxalic acid ester of formula (Ia):

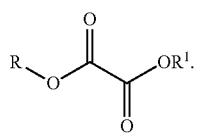
(Ia)

11. An emulsifier selected from the group consisting of an oxamate of formula (Ib), a hydroxycarbamate of formula (Ic), and a malonic acid ester of formula (Id):

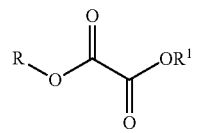
(Ia)

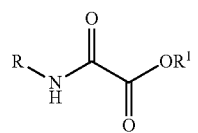
(Ib)

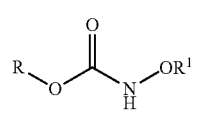
(Ic)

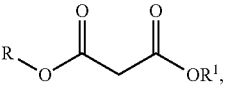
(Id)

wherein:
R is a saturated or a mono- or polyunsaturated, linear or branched hydrocarbon radical having 6 to 30 carbon atoms; and
$R^1$ is hydrogen or $C_1$-$C_4$-alkyl,
wherein for compound (Ic), $R^1$ is $C_{1-4}$ alkyl.

12. An emulsifier, comprising an oxalic acid ester of formula (Ia):

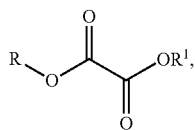
(Ia)

wherein:
R represents a linear $C_{10}$-, $C_{14}$-, $C_{16}$-$C_{18}$ or $C_{20}$-alkyl group; and
$R^1$ is hydrogen.

13. An emulsifier, consisting of an oxalic acid ester of formula (Ia):

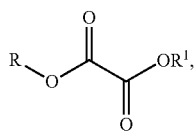
(Ia)

wherein:
R represents a linear $C_{10}$-, $C_{14}$-, $C_{16}$-, $C_{18}$- or $C_{20}$-alkyl group; and
$R^1$ is hydrogen.

14. The method of claim 1, wherein $R^2$ is a saturated or a mono- or polyunsaturated, linear or branched hydrocarbon radical having 6 to 30 carbon atoms.

15. The method according to claim 2, wherein the splitting of the emulsifier is effected by adding a base to the emulsion.

16. The method according to claim 15, wherein the emulsifier is an oxalic acid ester of formula (Ia):

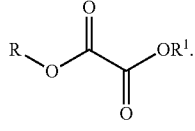
(Ia)

17. The method according to claim 2, wherein the splitting is effected by heating the emulsion to a temperature of from 50 to 200° C.

18. The method of claim 7, wherein $R^2$ is a saturated or a mono- or polyunsaturated, linear or branched hydrocarbon radical having 6 to 30 carbon atoms.

* * * * *